(12) United States Patent
Janka

(10) Patent No.: US 11,787,774 B2
(45) Date of Patent: *Oct. 17, 2023

(54) EFFICIENT PROCESS FOR PRODUCING 5-(ALKOXYCARBONYL)-FURAN-2-CARBOXYLIC ACIDS

(71) Applicant: Eastman Chemical Company, Kingsport, TN (US)

(72) Inventor: Mesfin Ejerssa Janka, Kingsport, TN (US)

(73) Assignee: Eastman Chemical Company, Kingsport, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/753,399

(22) PCT Filed: Aug. 25, 2020

(86) PCT No.: PCT/US2020/047716
§ 371 (c)(1),
(2) Date: Mar. 2, 2022

(87) PCT Pub. No.: WO2021/045927
PCT Pub. Date: Mar. 11, 2021

(65) Prior Publication Data
US 2022/0363654 A1  Nov. 17, 2022

Related U.S. Application Data

(60) Provisional application No. 62/896,178, filed on Sep. 5, 2019.

(51) Int. Cl.
C07D 307/68 (2006.01)

(52) U.S. Cl.
CPC .................. *C07D 307/68* (2013.01)

(58) Field of Classification Search
CPC ..................................................... C07D 307/68
USPC ........................................................ 549/485
See application file for complete search history.

(56) References Cited

U.S. PATENT DOCUMENTS

| | | | |
|---|---|---|---|
| 3,577,411 A | 5/1971 | Liechti et al. | |
| 3,584,039 A | 6/1971 | Meyer | |
| 3,996,271 A | 12/1976 | Yokota et al. | |
| 4,158,738 A | 6/1979 | Scott et al. | |
| 5,095,141 A | 3/1992 | Schammel et al. | |

(Continued)

FOREIGN PATENT DOCUMENTS

| | | |
|---|---|---|
| DE | 1146055 B | 3/1963 |
| EP | 2784069 A1 | 10/2014 |

(Continued)

OTHER PUBLICATIONS

Co-pending U.S. Appl. No. 16/430,628, filed Jun. 4, 2019, Janka.

(Continued)

*Primary Examiner* — Taylor V Oh
(74) *Attorney, Agent, or Firm* — Steven A. Owen (57) ABSTRACT

A process for preparing 5-(alkoxycarbonyl)furan-2-carboxylic acids (ACFC) by oxidizing various furcates in the presence of a catalyst containing cobalt, manganese, and bromine, and a solvent while simultaneously removing water vapor from the reaction chamber. The process can produce ACFC with high purity and low color, and in high yield.

18 Claims, 2 Drawing Sheets

(56) References Cited

U.S. PATENT DOCUMENTS

| | | | |
|---|---|---|---|
| 8,772,513 | B2 | 7/2014 | Janka et al. |
| 8,796,477 | B2 | 8/2014 | Janka et al. |
| 8,846,960 | B2 | 9/2014 | Janka et al. |
| 8,865,921 | B2 | 10/2014 | Munoz de Diego et al. |
| 9,156,805 | B2 | 10/2015 | Shaikh et al. |
| 9,206,149 | B2 | 12/2015 | Janka et al. |
| 9,765,045 | B2 | 9/2017 | Strensrud et al. |
| 10,344,011 | B1 | 7/2019 | Parker et al. |
| 10,421,736 | B2 | 9/2019 | Fontenot et al. |
| 10,526,301 | B1 | 1/2020 | Fontenot et al. |
| 10,544,118 | B2 * | 1/2020 | Janka ................ B01J 31/04 |
| 10,882,032 | B2 | 1/2021 | Fontenot et al. |
| 10,941,245 | B2 * | 3/2021 | Janka ................ C07D 307/68 |
| 11,440,895 | B2 * | 9/2022 | Janka ................ B01J 27/128 |
| 11,655,334 | B2 | 5/2023 | Janka et al. |
| 2005/0208582 | A1 | 9/2005 | Ohi et al. |
| 2006/0205977 | A1 | 9/2006 | Sumner, Jr. et al. |
| 2012/0059178 | A1 | 3/2012 | Sanborn |
| 2012/0283452 | A1 | 11/2012 | Munoz De Diego et al. |
| 2012/0302768 | A1 | 11/2012 | Janka et al. |
| 2012/0302769 | A1 | 11/2012 | Janka et al. |
| 2012/0302770 | A1 | 11/2012 | Janka et al. |
| 2012/0302771 | A1 | 11/2012 | Janka et al. |
| 2012/0302772 | A1 | 11/2012 | Shaikh et al. |
| 2012/0302773 | A1 | 11/2012 | Janka et al. |
| 2013/0345447 | A1 | 12/2013 | Shaikh et al. |
| 2013/0345448 | A1 | 12/2013 | Shaikh et al. |
| 2014/0066639 | A1 | 3/2014 | Janka et al. |
| 2014/0128623 | A1 | 5/2014 | Janka et al. |
| 2014/0128624 | A1 | 5/2014 | Janka et al. |
| 2015/0315166 | A1 | 11/2015 | Stensrud et al. |
| 2016/0024039 | A1 | 1/2016 | Mazoyer et al. |
| 2016/0207898 | A1 | 7/2016 | Singh et al. |
| 2016/0221980 | A1 | 8/2016 | Parker et al. |
| 2017/0313670 | A1 | 11/2017 | De Sousa Dias et al. |
| 2018/0155306 | A1 | 6/2018 | McKay et al. |
| 2019/0023677 | A1 | 1/2019 | Fontenot et al. |
| 2019/0031634 | A1 | 1/2019 | Metkar et al. |
| 2019/0389820 | A1 | 12/2019 | Janka |
| 2019/0389822 | A1 | 12/2019 | Janka |
| 2019/0389823 | A1 | 12/2019 | Janka |
| 2019/0389824 | A1 | 12/2019 | Janka |
| 2019/0389825 | A1 | 12/2019 | Janka |
| 2019/0389846 | A1 | 12/2019 | Janka |
| 2019/0390004 | A1 | 12/2019 | Janka |
| 2020/0123119 | A1 | 4/2020 | Fontenot et al. |

FOREIGN PATENT DOCUMENTS

| | | |
|---|---|---|
| WO | WO 2011/043660 A2 | 4/2011 |
| WO | WO 2011/043661 A1 | 4/2011 |
| WO | WO 2012-161967 A1 | 11/2012 |
| WO | WO 2016-126975 A1 | 8/2016 |
| WO | WO 2016-195499 A1 | 12/2016 |
| WO | WO 2016-202858 A1 | 12/2016 |
| WO | WO 2017-019441 A1 | 2/2017 |
| WO | WO 2017/076947 A1 | 5/2017 |
| WO | WO 2019/170204 A1 | 9/2019 |
| WO | WO 2021/045927 A1 | 3/2021 |

OTHER PUBLICATIONS

USPTO Office Action dated Jun. 11, 2020 received in co-pending U.S. Appl. No. 16/430,628 (U.S. Publication 2019-0389822).
USPTO Notice of Allowance dated Dec. 10, 2020 received in co-pending U.S. Appl. No. 16/430,628.
Co-pending U.S. Appl. No. 16/430,687, filed Jun. 4, 2019, Janka.
USPTO Office Action dated Mar. 9, 2020 received in co-pending U.S. Appl. No. 16/430,687 (U.S. Publication 2019-0389823).
USPTO Office Action dated Oct. 21, 2020 received in co-pending U.S. Appl. No. 16/430,687 (U.S. Publication 2019-0389823).
USPTO Office Action dated May 3, 2021 received in co-pending U.S. Appl. No. 16/460,687.
Co-pending U.S. Appl. No. 16/561,469, filed Sep. 5, 2019, Janka.
USPTO Office Action dated Apr. 10, 2020 received in co-pending U.S. Appl. No. 16/561,469 (U.S. Publication 2019-0389820).
USPTO Office Action dated Jan. 22, 2021 received in co-pending U.S. Appl. No. 16/561,469 (U.S. Publication 2019-0389820).
USPTO Office Action dated Sep. 28, 2021 received in co-pending U.S. Appl. No. 16/561,469.
Co-pending U.S. Appl. No. 16/561,484, filed Sep. 5, 2019, Janka.
USPTO Office Action dated Apr. 14, 2020 received in co-pending U.S. Appl. No. 16/561,484 (U.S. Publication 2019-0389846).
USPTO Office Action dated Oct. 9, 2020 received in co-pending U.S. Appl. No. 16/561,484 (U.S. Publication 2019-0389846).
USPTO Office Action dated Apr. 16, 2021 received in co-pending U.S. Appl. No. 16/561,484 (U.S. Publication 2019-0389846).
Co-pending U.S. Appl. No. 16/430,694, filed Jun. 4, 2019, Janka.
USPTO Office Action dated May 18, 2020 received in co-pending U.S. Appl. No. 16/430,694 (U.S. Publication 2019-0389824).
USPTO Office Action dated Sep. 8, 2020 received in co-pending U.S. Appl. No. 16/430,694 (U.S. Publication 2019-0389824).
USPTO Office Action dated Mar. 18, 2021 received in co-pending U.S. Appl. No. 16/430,694 (U.S. Publication 2019-0389824).
USPTO Office Action dated Jul. 22, 2021 received in co-pending U.S. Appl. No. 16/430,694.
UPSTO Office Action dated Dec. 9, 2021 received in co-pending U.S. Appl. No. 16/430,694.
USPTO Notice of Allowance dated May 4, 2022 received in co-pending U.S. Appl. No. 16/430,694.
Co-pending U.S. Appl. No. 16/430,607, filed Jun. 4, 2019, Janka.
Notice of Allowance dated Nov. 20, 2019 received in co-pending U.S. Appl. No. 16/430,607(Now U.S. Pat. No. 10,544,118).
Co-pending U.S. Appl. No. 16/430,704, filed Jun. 4, 2019, Janka.
USPTO Office Action dated Mar. 6, 2020 received in co-pending U.S. Appl. No. 16/430,704(U.S. Publication 2019-0389285).
USPTO Office Action dated Jul. 13, 2020 received in co-pending U.S. Appl. No. 16/430,704 (U.S. Publication 2019-0389825).
USPTO Office Action dated Nov. 13, 2020 received in co-pending U.S. Appl. No. 16/430,704 (U.S. Publication 2019-0389825).
USPTO Office Action dated Mar. 19, 2021 received in co-pending U.S. Appl. No. 16/430,704 (U.S. Publication 2019-0389825).
USPTO Office Action dated Jul. 28, 2021 received in co-pending U.S. Appl. No. 16/430,704.
Co-pending U.S. Appl. No. 16/430,717, filed Jun. 4, 2019, Janka.
USPTO Office Action dated Apr. 15, 2021 received in co-pending U.S. Appl. No. 16/430,717.
USPTO Office Action dated Nov. 8, 2021 received in co-pending U.S. Appl. No. 16/430,717.
USPTO Office Action dated Mar. 10, 2022 received in co-pending U.S. Appl. No. 16/430,717.
Notification of Transmittal of The International Search Report and The Written Opinion of the International Searching Authority, or the Declaration; International Application No. PCT/US2019/037427 with a filing date of Jun. 17, 2019.
Notification of Transmittal of The International Search Report and The Written Opinion of the International Searching Authority, or the Declaration; International Application No. PCT/US2020/047716 with a filing date of Dec. 4, 2020.
Gandini, Alessandro, et al.; "The Furan Counterpart of Poly(ethylene terephthalate): An Alternative Material Based on Renewable Resources"; Journal of Polymer Science: Part A: Polymer Chemistry, vol. 47, (2009), pp. 295-298.
Moraes, Maria De Lourdes L., et al., "Analysis of impurities in crude and highly-purified terephthalic acid by capillary electrophoresis", Journal of the Brazilian Chemical Society, 2004, vol. 15, No. 3, pp. 400-406.
Shen, Yong, et al.; "Facile preparation of bio-based polyesters from furandicarboxylic acid and long chain diols via asymmetric monomer strategy"; Green Chem., 2017, 19, 4930-4938.
Langolf, Sebastian, et al.; Development of Antitrypanosomal and Antiplasmodial Nonpeptidic Cysteine Inhibitors based on N-Protected-Guanidino-Furan and -Pyrrole Building Blocks; ChemMedChem, 2011, 6, pp. 1581-1586.

(56) References Cited

OTHER PUBLICATIONS

Schmuck, Carsten, et al.; 2-(Guanidiniocarbonyl)furans as a New Class of Potential Anion Hosts: Synthesis and First Binding Studies; European Journal of Organic Chemistry, 2006, 19, pp. 4385-4392.
Zuo, Xiaobin, et al.; Optimization of Co/Mn/Br-Catalyzed Oxidation of 5-Hydroxymethylfurfural to Enhance 2,5-Furandicarboxylic Acid Yield and Minimize Substrate Burning; ACS Sustainable Chem. Eng., 2016, vol. 4, pp. 3659-3668.
Partenheimer, Walt, et al.; "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts"; Advanced Synthetic Catal., 2001, 343, No. 1, 102-111.
Tojo, Gabriel et al.; "Oxidation of Primary Alcohols to Carboxylic Acids", Chapter 1, Springer, 2007, 17 pages.
Deng, Jin et al.; Aerobic Oxidation of Hydroxymethylfurfural and Furfural by Using Heterogeneous $Co_xO_y$—N@C Catalysts; Chemsuschem, 2014, 7, pp. 3334-3340.
Notice of Allowance dated Mar. 1, 2023 received in co-pending U.S. Appl. No. 16/430,717.

\* cited by examiner

EFFICIENT PROCESS FOR PRODUCING 5-(ALKOXYCARBONYL)-FURAN-2-CARBOXYLIC ACIDS

CROSS-REFERENCE TO RELATED APPLICATION(S)

This application is a national stage filing under 35 USC § 371 of International Application Number PCT/US2020/047716, filed on, Aug. 25, 2020, which claims the benefit of the filing date to U.S. Provisional Application No. 62/896,178, filed on Sep. 5, 2019, the entire disclosures of which are incorporated by reference herein.

TECHNICAL FIELD

The invention generally relates to the field of organic chemistry. It particularly relates to an efficient process for preparing 5-(alkoxycarbonyl)furan-2-carboxylic acids (ACFC).

BACKGROUND

Aromatic dicarboxylic acids, such as terephthalic acid and isophthalic acid, are used to produce a variety of polyesters. Examples of such polyesters include polyethylene terephthalate (PET) and its copolymers. These aromatic dicarboxylic acids are typically synthesized by catalytically oxidizing the corresponding dialkyl aromatic compounds, which are obtained from fossil fuels.

There is a growing interest in using renewable resources as feedstocks in the chemical industry, mainly due to the progressive reduction of fossil reserves and their related environmental impact. Furan-2,5-dicarboxylic acid (FDCA) and ACFC are versatile intermediates considered to be promising, closest bio-based alternatives to terephthalic acid and isophthalic acid. Like aromatic diacids, ACFC and FDCA can be condensed with diols, such as ethylene glycol, to make polyester resins similar to PET.

Thus, there is a need in the art to provide alternative and/or improved processes for producing carboxylic acid compositions, especially those containing ACFC.

The present invention addresses this need as well as others, which will become apparent from the following description and the appended claims.

SUMMARY

The invention is as set forth in the appended claims.

Briefly, the invention provides a process for preparing a compound of the structural formula (I):

(I)

The process comprises the steps of:
(a) reacting a compound of the structural formula (II):

(II)

with an oxidizing agent in a reactor comprising an oxidation catalyst and a solvent; and
(b) removing water vapor from the reactor while the reaction is occurring.

The oxidation catalyst comprises cobalt, manganese, and bromine.

The solvent comprises a monocarboxylic acid having 2 to 6 carbon atoms.

$R^1$ is hydrogen, $R^3O—$, or $R^3C(O)O—$.

$R^2$ is an alkyl group having 1 to 6 carbon atoms.

$R^3$ is hydrogen or an alkyl group having 1 to 6 carbon atoms.

DETAILED DESCRIPTION

In one aspect, the invention provides a process for preparing a compound of the structural formula (I):

(I)

where $R^2$ is an alkyl group having 1 to 6 carbon atoms. The alkyl group may be branched or straight-chained. Examples of such groups include methyl, ethyl, propyl, isopropyl, butyl, methylpropyl, pentyl, ethylpropyl, hexyl, methylpentyl, and ethylbutyl.

In various embodiments, $R^2$ is an alkyl group having 1 to 3 carbon atoms.

In various other embodiments, $R^2$ is methyl.

The compound (I) may be referred to as 5-(alkoxycarbonyl) furan-2-carboxylic acid (ACFC). When $R^2$ is methyl, the compound (I) is 5-(methoxycarbonyl)furan-2-carboxylic acid (MCFC).

The process for preparing compound (I) comprises the steps of:
(a) reacting a compound of the structural formula (II):

(II)

with an oxidizing agent in a reactor comprising an oxidation catalyst and a solvent; and
  (b) removing water vapor from the reactor while the reaction is occurring.

$R^1$ in formula (II) is hydrogen, $R^3O—$, or $R^3C(O)O—$ where $R^3$ is hydrogen or an alkyl group having 1 to 6 carbon atoms. As with $R^2$, the alkyl group in $R^3$ may be branched or straight-chained.

In various embodiments, $R^3$ is hydrogen or an alkyl group having 1 to 3 carbon atoms.

In various other embodiments, $R^1$ is hydrogen.

In yet various other embodiments, $R^1$ is $R^3O—$ where $R^3$ is hydrogen, methyl, ethyl, propyl, or isopropyl.

In yet various other embodiments, $R^1$ is $R^3C(O)O—$ where $R^3$ is hydrogen, methyl, ethyl, propyl, or isopropyl.

$R^2$ in formula (II) is the same as that in formula (I), i.e., an alkyl group having 1 to 6 carbon atoms, or 1 to 3 carbon atoms, or methyl.

Specific examples of the compounds (II) include the following:

methyl 5-methylfuran-2-carboxylate (MMFC)

methyl 5-(hydroxymethyl)furan-2-carboxylate methyl 5-(methoxymethyl)furan-2-carboxylate methyl 5-(ethoxymethyl)furan-2-carboxylate ethyl 5-methylfuran-2-carboxylate ethyl 5-(hydroxymethyl)furan-2-carboxylate ethyl 5-(methoxymethyl)furan-2-carboxylate ethyl 5-(ethoxymethyl)furan-2-carboxylate propyl 5-methylfuran-2-carboxylate propyl 5-(hydroxymethyl)furan-2-carboxylate propyl 5-(methoxymethyl)furan-2-carboxylate propyl 5-(ethoxymethyl)furan-2-carboxylate isopropyl 5-methylfuran-2-carboxylate isopropyl 5-(hydroxymethyl)furan-2-carboxylate isopropyl 5-(methoxymethyl)furan-2-carboxylate isopropyl 5-(ethoxymethyl)furan-2-carboxylate methyl 5-((formyloxy)methyl)furan-2-carboxylate In various embodiments, the compound (II) may be selected from methyl 5-methylfuran-2-carboxylate (MMFC), methyl 5-(hydroxymethyl) furan-2-carboxylate, methyl 5-(methoxymethyl)furan-2-carboxylate, methyl 5-(ethoxymethyl)furan-2-carboxylate, ethyl 5-methylfuran-2-carboxylate, ethyl 5-(hydroxymethyl)furan-2-carboxylate, ethyl 5-(methoxymethyl) furan-2-carboxylate, ethyl 5-(ethoxymethyl)furan-2-carboxylate, propyl 5-methyl-furan-2-carboxylate, propyl 5-(hydroxymethyl)furan-2-carboxylate, propyl 5-(methoxymethyl)furan-2-carboxylate, propyl 5-(ethoxymethyl) furan-2-carboxylate, isopropyl 5-methylfuran-2-carboxylate, isopropyl 5-(hydroxymethyl) furan-2-carboxylate, isopropyl 5-(methoxymethyl) furan-2-carboxylate, methyl 5-((formyloxy)methyl)furan-2-carboxylate, methyl 5-(acetoxymethyl)furan-2-cayboxylate, methyl 5-((propionyloxy)methyl) furan-2-carboxylate, ethyl 5-((formyloxy)methyl)furan-2-carboxylate, ethyl 5-(acetoxymethyl)furan-2-cayboxylate, ethyl 5-((propionyloxy) methyl) furan-2-carboxylate, propyl 5-((formyloxy)methyl) furan-2-carboxylate, propyl 5-(acetoxymethyl)furan-2-cayboxylate, propyl 5-((propionyloxy)methyl) furan-2-carboxylate, isopropyl 5-((formyloxy)methyl)furan-2-carboxylate, isopropyl 5-(acetoxymethyl)furan-2-cayboxylate, isopropyl 5-((propionyloxy)methyl) furan-2-carboxylate, isopropyl 5-(ethoxymethyl)furan-2-carboxylate, and mixtures thereof.

In various other embodiments, the compound (II) may be selected from methyl 5-methylfuran-2-carboxylate (MMFC), methyl 5-(hydroxymethyl)furan-2-carboxylate, methyl 5-(methoxymethyl) furan-2-carboxylate, methyl 5-(ethoxymethyl)furan-2-carboxylate, methyl 5-((formyloxy)methyl)furan-2-carboxylate, methyl 5-(acetoxymethyl) furan-2-cayboxylate, methyl 5-((propionyloxy)methyl) furan-2-carboxylate, and mixtures thereof.

In yet various other embodiments, the compound (II) includes methyl 5-methylfuran-2-carboxylate (MMFC).

The compound (II) may be prepared from renewable feedstocks by literature methods and/or may be obtained commercially, such as from xF Technologies Inc.

The oxidizing agent useful in the present process is not particularly limiting. It refers to a source of oxygen. Preferably, the oxidizing agent is an oxygen-containing gas. Examples include molecular oxygen, air, and other oxygen-containing gas. The oxygen-containing gas introduced into the reactor can have from 5 to 80 mole %, from 5 to 60 mole %, from 5 to 45 mole %, or from 15 to 25 mole % of molecular oxygen. The balance of the oxygen-containing gas may be one or more gases inert to oxidation, such as nitrogen and argon.

The oxidation catalyst comprises cobalt, manganese, and bromine. The cobalt, manganese, and bromine may be supplied by any suitable source. The catalyst components are typically sourced from compounds that are soluble in the solvent under reaction conditions or are soluble in the reactant(s) fed to the oxidation zone. Preferably, the sources of the catalyst components are soluble in the solvent at 25°

C., 30° C., or 40° C., and 1 atm, and/or are soluble in the solvent under reaction conditions.

The cobalt may be provided in ionic form as inorganic cobalt salts, such as cobalt bromide, cobalt nitrate, or cobalt chloride; or as organic cobalt compounds, such as cobalt salts of aliphatic or aromatic acids having 2-22 carbon atoms, including cobalt acetate, cobalt octanoate, cobalt benzoate, cobalt acetylacetonate, and cobalt naphthalate.

The oxidation state of cobalt when added as a compound to the reaction mixture is not limited and includes both the +2 and +3 oxidation states.

The manganese may be provided as one or more inorganic manganese salts, such as manganese borates, manganese halides, manganese nitrates; or as organometallic manganese compounds, such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrogen bromide, hydrobromic acid (sometimes referred to as aqueous hydrogen bromide or aqueous HBr), sodium bromide, potassium bromide, ammonium bromide, and tetrabromoethane. Hydrobromic acid or sodium bromide may be preferred bromine sources.

The cobalt can used in amounts ranging from 2 to 10,000 ppmw, from 500 to 6,000 ppmw, from 1,000 to 6,000 ppmw, from 700 to 4,500 ppmw, or from 1,000 to 4,000 ppmw.

The manganese can be used in amounts ranging from 2 to 10,000 ppmw, from 2 to 600 ppmw, from 20 to 400 ppmw, or from 20 to 200 ppmw.

The bromine can be used in amounts ranging from 2 to 10,000 ppmw, from 300 to 4,500 ppmw, from 700 to 4,000 ppmw, or from 1,000 to 4,000 ppmw.

These exemplary ranges of Co, Mn, and Br are based on the total weight of the reaction mixture.

Alternatively, the catalyst amounts may be expressed based on the weight of the raw material, i.e., the compound (II). In which case, the reaction may be performed with, for example, a cobalt content of 0.50 to 5.0 wt %, an Mn content of 0.15 to 3.0 wt %, and a Br content of 0.11 to 3.2 wt %, based on the weight of compound (II).

In various embodiments, the cobalt content can range from 0.50 to 1.0 wt %, the Mn content can range from 1.5 to 2.3 wt %, and the bromine content can range from 0.32 to 3.2 wt %, based on the weight of compound (II).

In various embodiments, the weight ratio of cobalt to manganese in the oxidation catalyst can be at least 0.01:1, at least 0.1:1, at least 1:1, at least 10:1, at least 20:1, at least 50:1, at least 100:1, or at least 400:1.

In various other embodiments, the weight ratio of Co:Mn in the oxidation catalyst can range from 1:1 to 400:1, from 10:1 to 400:1, or from 20:1 to 400:1.

In yet various other embodiments, the weight ratio of Co:Mn in the oxidation catalyst can range from 0.1:1 to 100:1, from 0.1:1 to 10:1, from 0.1:1 to 1:1, from 1:1 to 100:1, from 10:1 to 100:1, or from 20:1 to 100:1.

In various embodiments, the weight ratio of cobalt to bromine can vary from 0.7:1 to 3.5:1, from 0.5:1 to 10:1, or from 0.5:1 to 5:1.

The above ratios of Co:Mn and Co:Br can generate a high yield of ACFC, decrease the formation of impurities, including those causing color in the product (as measured by b*), and/or keep the amount of CO and $CO_2$ in the off-gas to a minimum.

The solvent for the reaction comprises a monocarboxylic acid having 2 to 6 carbon atoms or from 2 to 4 carbon atoms. Examples of such acids include acetic acid, propionic acid, n-butyric acid, isobutyric acid, n-valeric acid, trimethylacetic acid, and caprioic acid. Mixtures of such acids may be used as well as mixtures of one or more of the acids with water. The solvent may be selected based on its ability to solubilize the catalyst components under the reaction conditions. The solvent may also be selected based on its volatility under the reaction conditions so as to allow it to be taken as an off-gas from the oxidation reactor either separately or together with the water vapor.

In various embodiments, the solvent comprises anhydrous acetic acid, mixtures of peracetic acid and acetic acid, mixtures of acetic acid and water, or mixtures of peracetic acid, acetic acid, and water.

In various other embodiments, the solvent used for the oxidation is an aqueous acetic acid solution, typically having a concentration of 50 to 99 wt %, 75 to 99 wt %, or 80 to 99 wt % of acetic acid.

The solvent and catalyst used in the process may be recycled and reused. For example, a crude ACFC composition may be discharged from the oxidation reactor and subjected to a variety of mother liquor exchange, separation, purification, and/or recovery methods. These methods can provide recovered solvent and catalyst components for recycling back to the oxidation reactor. Thus, a portion of the solvent introduced into the oxidation reactor may be from a recycle stream obtained by displacing, for example, from 80 to 90 wt % of the mother liquor in the crude reaction mixture discharged from the oxidation reactor. The mother liquor may be displaced with fresh, wet acetic acid, for example, acetic acid containing from greater than 0 to 20 wt %, or from greater than 0 to 15 wt %, of water.

Generally, the oxidation reaction can be carried out at a temperature from 50° C. to 220° C., from 75° C. to 200° C., from 75° C. to 180° C., from 100° C. to 200° C., from 100° C. to 180° C., from 110° C. to 180° C., from 130° C. to 180° C., from 100° C. to 160° C., from 110° C. to 160° C., or from 130° C. to 160° C. The typical oxidization reactor can be characterized by a lower section where gas bubbles are dispersed in a continuous liquid phase. Solids can also be present in the lower section. In the upper section of the reactor, gas is the continuous phase where entrained liquid drops can also be present. These oxidation temperatures refer to the temperature of the reaction mixture inside the oxidation reactor where liquid is present as the continuous phase.

In various embodiments, the liquid phase in the oxidation reactor has a pH from −4.0 to 2.0.

Generally, the oxidation reaction can be carried out with a pressure above the reaction mixture of, for example, 50 to 1,000 psig, 50 to 750 psig, 50 to 500 psig, 50 to 400 psig, 50 to 200 psig, 100 to 1000 psig, 100 to 750 psig, 100 to 500 psig, 100 to 400 psig, 100 to 300 psig, or 100 to 200 psig. The pressure is typically selected such that the solvent is mainly in the liquid phase.

The oxidation process may be carried out in a batch, semi-continuous (sometimes referred to as semi-batch), or continuous mode. A batch process typically involves adding the entire amount of the compound (II) feedstock, the catalyst, and the solvent into the reactor before starting the reaction, passing an oxidizing gas through the reaction mixture to initiate and perform the reaction, and recovering the reaction mixture all at once at the end of the reaction.

A semi-continuous process typically involves adding the entire amount of the catalyst and the solvent into the reactor, continuously introducing the compound (II) feedstock and the oxidizing gas to the reactor to carry out the oxidation reaction, and recovering the reaction mixture all at once at the end of the reaction.

A continuous process typically involves continuously introducing the raw material, the catalyst, the solvent, and the oxidizing gas into the reactor to carry out the oxidation reaction and continuously recovering the reaction mixture containing the product compound (I).

The oxidation reaction time can vary, depending on various factors such as the temperature, pressure, and catalyst composition/concentration employed. But typically, the reaction time can range from 1 to 6 hours or from 1 to 3 hours.

The present process can produce compound (I) in a yield of at least 50%, at least 60%, at least 70%, at least 80%, at least 85%, at least 90%, at least 95%, at least 98%, at least 99%, or at least 99.5%.

Yield can be calculated by dividing the mass of the ACFC (compound (I)) obtained by the theoretical amount of the oxidable raw material (compound (II)) that should be produced based on the amount of raw material that has been consumed. For example, in the case of MMFC as the compound (II), if one mole or 140.1 grams of MMFC are oxidized, it would theoretically generate one mole or 170.1 grams of MCFC. If, for example, the actual amount of MCFC formed is only 150 grams, the yield of MCFC for this reaction would be 88.2% (=150/170.1×100). The same calculation can be made for an oxidation reaction using other oxidizable compounds as well as to other products/byproducts.

In addition to the compound (I), the present process can produce one or more byproducts. These byproducts can include furan-2,5-dicarboxylic acid (FDCA), 5-formylfuran-2-carboxylic acid (FFCA), and alkyl 5-formylfuran-2-carboxylate (AFFC). When $R^2$ in the starting compound (II) is methyl, the AFFC is methyl 5-formylfuran-2-carboxylate (MFFC). The structural formulas of FDCA, FFCA, AFFC, and MFFC are provided below.

In addition to the compound (I) and byproducts, the oxidation reaction generates water. Without wishing to be bound by theory, it is believed that the presence of water in the reaction mixture tends to induce the formation of one or more byproducts at elevated reaction temperatures. To minimize the formation of byproducts, such as FDCA, especially at the higher operating temperatures, the present process includes the step of removing water, in the form of vapor, from the oxidation reactor while the reaction is running, thereby reducing the amount of water that is present in the reaction mixture.

To facilitate water evaporation from the reaction mixture and its removal from the reactor, the reaction may be carried out at a pressure lower than the vapor pressure of water at the chosen reaction temperature to evaporate the water formed by the reaction. For example, for reaction temperatures of 200° C. or less, such as 130° C. to 180° C., the reaction pressure may be in the range of 30 psig to 250 psig, 30 psig to 150 psig, 30 to 100 psig, 50 psig to 250 psig, 50 psig to 150 psig, or 50 psig to 100 psig.

Depending on the oxidation solvent composition and the conditions employed, a portion of the solvent may evaporate along with the water formed by the reaction. In which case, the removing step (b) may include withdrawing a gaseous stream comprising solvent vapor and water vapor from the reactor. For example, in the case the solvent comprises acetic acid, which has a boiling point close to that of water, a portion of the acetic acid may evaporate along with the water. Both the solvent vapor and the water vapor may be withdrawn from the reactor in the same stream, condensed and/or separated, and the solvent may be returned to the reactor for reuse.

Figure 2:
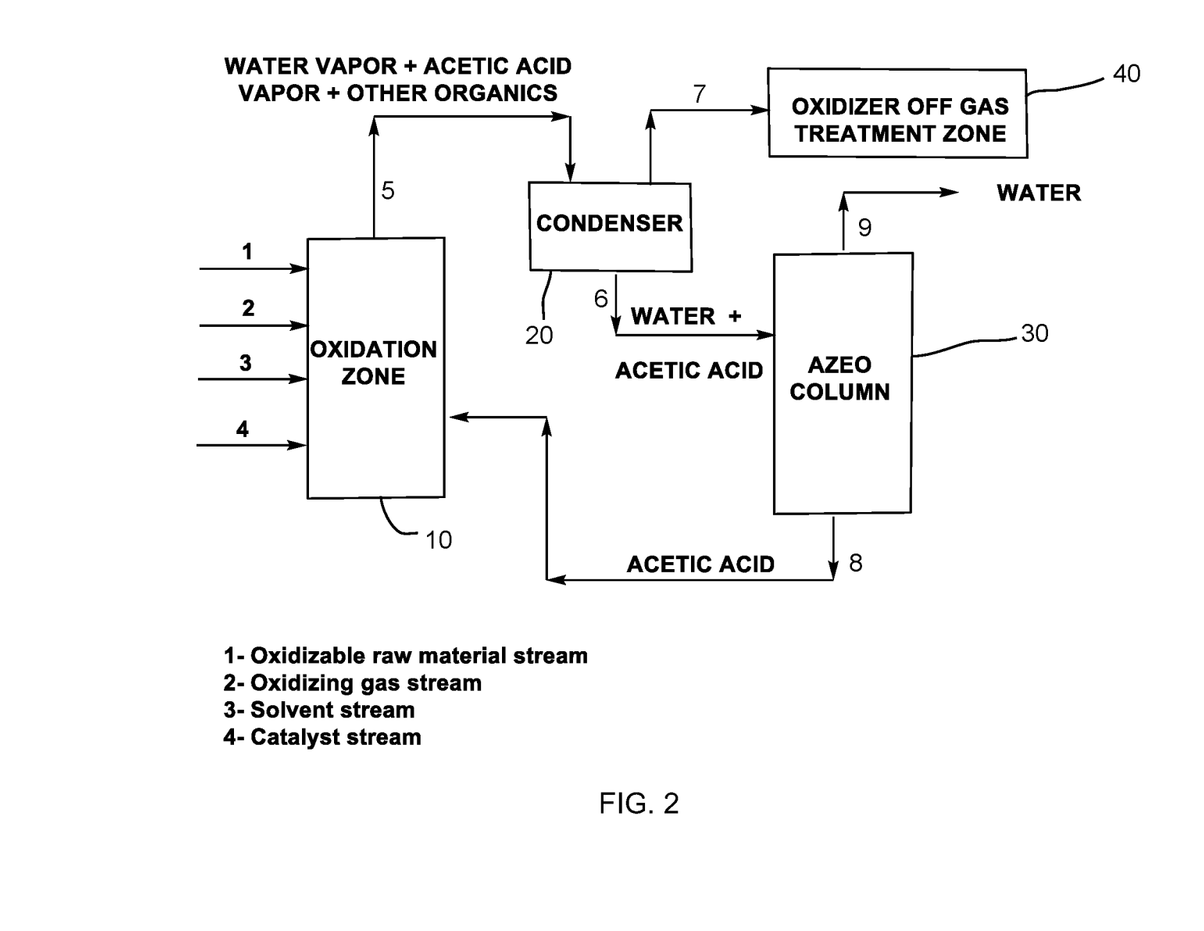
FIG. 2 is a flow diagram of a process for oxidizing compound (II) with water removal from the oxidation zone according to an embodiment of the invention.

To further illustrate the invention, FIG. 2 is provided. FIG. 2 shows a flow diagram of a possible implementation of a process according to the invention with acetic acid as the solvent.

In FIG. 2, an oxidizable raw material stream 1 comprising a furoate of compound (II); an oxidizing gas stream 2 comprising, for example, air; a solvent stream 3 comprising acetic acid; and a catalyst stream 4 are introduced into oxidation zone (OZ) 10. While streams 1, 2, 3, and 4 are shown as separate, individual feeds, they may be mixed or combined in any combination prior to being introduced into the OZ 10. Streams 1, 2, 3, and 4 may enter at a single location or at multiple locations in the OZ 10.

Under oxidation reaction conditions, a vapor phase is formed in the OZ 10. The vapor phase typically comprises water vapor (from water formed during the reaction), acetic acid vapor, and possibly other volatile organic compounds (VOCs). At least a portion of the vapor phase in the OZ 10 is withdrawn as a gaseous stream 5. Stream 5 may then be passed to a condenser 20 to condense at least a portion of the water vapor and the acetic acid vapor to form a liquid stream 6.

The liquid stream 6 comprising water and acetic acid may then be passed to an azeotropic distillation column 30 where it is mixed with a suitable entrainer (e.g., ethyl n-valerate or 4-methyl-2-pentanone) (not shown) to separate the water from the acetic acid. Although azeotropic distillation is shown in FIG. 2, any other acetic acid/water separation technique may be used, such as extractive distillation, liquid-liquid extraction, adsorption with molecular sieves, and membrane separation.

The column 30 generates a water-enriched stream 9, which may be withdrawn as an overhead stream, and an acetic acid-enriched stream 8, which may be withdrawn as a bottoms stream. The acetic acid-enriched stream 8 may then be recycled back to the OZ 10 for further use.

The remaining vapor in condenser 20 may be removed via line 7 and passed to an oxidizer off-gas treatment zone 40 for further processing such as separation, purification, and/or discharge.

By removing water, in the form of vapor, during the oxidation reaction, the solvent/reaction mixture at the end of the reaction contains very little water, for example, 2 wt % or less, 1.5 wt % or less, 1.3 wt % or less, 1.2 wt % or less, or 1.1 wt % or less of water, based on the total weight of the solvent/reaction mixture.

By removing water, in the form of vapor, during the oxidation reaction, the present process can produce less byproducts, such as FDCA, compared to a process carried out under the same reaction conditions but without performing the removing step (b).

In various embodiments, the present process produces FDCA in yields of less than 20%, less than 15%, less than 10%, less than 5%, less than 1%, or less than 0.5%.

In the present process, the extent of solvent burned and rendered unusable, as estimated by carbon oxides formation, can be the same as, or even lower than, typical oxidation processes. Even though the absolute amount of carbon oxides formation may be reduced by known techniques, this reduction can be achieved without risking an acceptable conversion. Obtaining a low amount of carbon oxides formation may generally be achieved by running the reaction at lower oxidation temperatures and/or using a catalyst that has a lower degree of conversion or selectivity, but this typically results in decreased conversion and increased quantities of intermediates. The present process, however, can have the advantage of maintaining a low ratio of solvent burn to conversion, thereby minimizing the impact on conversion to obtain the low solvent burn relative to other oxidation processes.

Thus, in various embodiments, the ratio of carbon oxides formation (in moles of CO and $CO_2$ expressed as $CO_x$, per mole of compound (II) feed), can be no more than 1.0 mole $CO_x$, or no more than 0.5 mole $CO_x$, or no more than 0.3 mole $CO_x$, in each case with respect to the molar quantity of the compound (II) fed into the reactor.

At the end of the reaction, the reaction mixture is typically depressurized and cooled to obtain a slurry comprising the product compound (I). The product slurry may undergo one or more solid-liquid separation (such as filtration and/or centrifugation) and washing steps to obtain a wet cake. The wet cake may then be dried (optionally at elevated temperature and under vacuum) to obtain a dried, solid product composition.

In various embodiments, the present process may include one or more steps to obtain a dried, solid product composition comprising the compound (I).

These steps include at the conclusion of the oxidation reaction, passing at least a portion of the oxidation reaction mixture to a crystallization zone to form a crystallized slurry. Generally, the crystallization zone comprises at least one crystallizer. In the crystallization zone, the reaction mixture may be cooled to a temperature from 20° C. to 175° C., 40° C. to 175° C., 50° C. to 170° C., 60° C. to 165° C., 25° C. to 100° C., or from 25° C. to 50° C., to form the crystallized slurry. Vapor from the crystallization zone can be condensed in at least one condenser and returned to the crystallization zone or routed away from crystallization zone. Alternatively, vapor from the crystallization zone can be recycled without condensation or sent to an energy recovery device. As another option, the crystallizer vapor can be withdrawn and routed to a recovery system where the solvent is removed and recycled, and any VOCs may be treated, for example, by incineration in a catalytic oxidation unit.

The crystallized slurry may be further cooled in a cooling zone to generate a cooled, crystallized slurry. The cooling can be accomplished by any means known in the art. Typically, the cooling zone comprises a flash tank. The temperature of the cooled, crystallized slurry can range from 20° C. to 160° C., from 35° C. to 160° C., from 20° C. to 140° C., from 50° C. to 140° C., from 20° C. to 120° C., from 25° C. to 120° C., from 45° C. to 120° C., from 70° C. to 120° C., from 55° C. to 95° C., from 75° C. to 95° C., or from 20° C. to 70° C.

In various embodiments, at least a portion (up to 100%) of the oxidation mixture can be routed directly to the cooling zone without first passing through the crystallization zone.

In various other embodiments, at least a portion (up to 100%) of the crystallized slurry can be routed directly to a solid-liquid separation zone without first passing through the cooling zone.

The cooled, crystallized slurry may be passed to a solid-liquid separation zone. The solid-liquid separation zone typically comprises one or more solid-liquid separation devices configured to separate solids from liquids. In the solid-liquid separation zone, the solids may be washed with a wash solvent and dewatered by reducing the moisture content in the washed solids to less than 30 wt %, less than 25 wt %, less than 20 wt %, less than 15 wt %, or less than 10 wt %.

Equipment suitable for the solid-liquid separation zone typically include centrifuges, cyclones, rotary drum filters, belt filters, pressure leaf filters, candle filters, etc.

In various embodiments, the solid-liquid separation zone includes a rotary pressure drum filter.

The wash solvent comprises a liquid suitable for displacing and washing mother liquor from the solids.

In various embodiments, the wash solvent comprises acetic acid and water.

In various other embodiments, the wash solvent comprises water (up to 100%).

The temperature of the wash solvent can range from 20° C. to 135° C., from 40° C. to 110° C., from 50° C. to 90° C., or from 20° C. to 70° C. The amount of wash solvent used can be characterized as the wash ratio, which corresponds to the mass of the wash liquid divided by the mass of the solids on a batch or continuous basis. The wash ratio can range from 0.3 to 5, from 0.4 to 4, or from 0.5 to 3.

After the solids are washed in the solid-liquid separation zone, they are typically dewatered to generate a purified, wet cake. Dewatering involves reducing the moisture content of the solids to less than 30 wt %, less than 25 wt %, less than 20 wt %, less than 15 wt %, or less than 10 wt %.

In various embodiments, dewatering is accomplished in a filter by passing a gas stream through the solids to displace free liquid after the solids have been washed with a wash solvent.

In various other embodiments, dewatering is achieved by centrifugal forces in a perforated-or solid-bowl centrifuge.

The filtrate generated in the solid-liquid separation zone is a mother liquor comprising the oxidation solvent, the catalyst, and some impurities/oxidation byproducts. The filtrate can be routed to a purge zone or back to the oxidation reactor or both.

In the purge zone, a portion of the impurities present in the mother liquor can be isolated and removed. The remaining solvent and catalyst can be isolated and recycled to the oxidation reactor.

In various embodiments, the remaining solvent from the purge zone can contain greater than 30%, greater than 50%, greater than 70%, or greater than 90% of the catalyst that entered the purge zone on a continuous or batch basis.

Wash liquor from the solid-liquid separation zone typically comprises a portion of the mother liquor and wash solvent. The ratio of mother liquor mass to wash solvent mass can be less than 3 or less than 2.

The purified, wet cake from the solid-liquid separation zone may be passed to a drying zone to generate a dry, solid product and a vapor stream. The vapor stream can comprise wash solvent vapor and/or oxidation solvent vapor.

The drying zone typically comprises one or more dryers capable of evaporating at least 10% of the volatiles remaining in the purified, wet cake. Examples of such dryers include indirect contact dryers, such as rotary steam tube dryers, Single-Shaft Porcupine™ dryers, and Bepex Solidaire™ dryers as well as direct contact dryers, such as fluidized-bed dryers and ovens equipped with conveyers.

In various embodiments, a vacuum system can be used to draw the vapor stream from the drying zone. If a vacuum system is used in this fashion, the pressure of the vapor stream at the dryer outlet can range from 760 mm Hg to 400 mm Hg, from 760 mm Hg to 600 mm Hg, from 760 mm Hg to 700 mm Hg, from 760 mm Hg to 720 mm Hg, or from 760 mm Hg to 740 mm Hg, where the pressure is measured in mm Hg above absolute vacuum.

The process according to the invention can produce a dried, solid product containing the compound (I) that is surprisingly pure and low in color, without the need to perform reactive purification steps, such as secondary oxidations (sometimes referred to as post-oxidation), hydrogenations, and/or treatments with an oxidizer (such as sodium hypochlorite and/or hydrogen peroxide).

In a batch process, secondary oxidation refers to the step of continuing to supply the oxidizing gas to the reactor after the absorption of oxygen in the reaction medium has stopped. In a semi-continuous or continuous process, secondary oxidation refers to the step of continuing to supply of the oxidizing gas to the reaction zone when the supply of the compound (II) feedstock is stopped.

Thus, in a second aspect, the invention provides a dried, solid composition comprising at least 70 wt % of a compound of the structural formula (I):

(I)

wherein $R^2$ is defined herein above and the wt % of compound (I) is based on the total weight of the composition.

In various embodiments, the dried, solid composition comprises at least 80 wt %, at least 90 wt %, at least 95 wt %, at least 97 wt %, at least 98 wt %, at least 99 wt %, or at least 99.5 wt % of the compound (I), based on the total weight of the composition.

In various embodiments, the dried, solid composition comprises less than 30 wt %, less than 20 wt %, less than 10 wt %, less than 5 wt %, less than 3 wt %, less than 2 wt %, less than 1 wt %, or less than 0.05 wt % of furan-2,5-dicarboxylic acid (FDCA), based on the total weight of the composition. In each case, the content of FDCA may be greater than 0 wt %.

In various embodiments, the dried, solid composition comprises less than 1 wt %, less than 0.5 wt %, less than 0.3 wt %, less than 0.1 wt %, less than 500 ppmw, less than 400 ppmw, less than 300 ppmw, less than 200 ppmw, less than 100 ppmw, less than 50 ppmw, less than 10 ppmw, less than 5 ppmw, or less than 1 ppmw of 5-formylfuran-2-carboxylic acid (FFCA), based on the total weight of the composition. In each case, the content of FFCA may be greater than 0 wt %.

In various embodiments, the dried, solid composition comprises less than 1 wt %, less than 0.5 wt %, less than 0.3 wt %, less than 0.1 wt %, less than 500 ppmw, less than 400 ppmw, less than 300 ppmw, less than 200 ppmw, less than 100 ppmw, less than 50 ppmw, or less than 10 ppmw of alkyl 5-formylfuran-2-carboxylate (AFFC), based on the total weight of the composition. In each case, the content of AFFC may be greater than 0 wt %.

When $R^2$ is methyl in compound (I), the dried, solid composition comprises less than 1 wt %, less than 0.5 wt %, less than 0.3 wt %, less than 0.1 wt %, less than 500 ppmw, less than 400 ppmw, less than 300 ppmw, less than 200 ppmw, less than 100 ppmw, less than 50 ppmw, or less than 10 ppmw of methyl 5-formylfuran-2-carboxylate (MFFC), based on the total weight of the composition. In each case, the content of MFFC may be greater than 0 wt %.

In various embodiments, the dried, solid composition can have a b* value of less than 4, less than 2, less than 1, from −1 to +1, or from −0.5 to +0.5.

The b* value is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow).

In one embodiment, the dried, solid composition comprises:
 (a) at least 70 wt % of a compound (I);
 (b) less than 30 wt % of furan-2,5-dicarboxylic acid (FDCA);
 (c) less than 500 ppmw of 5-formylfuran-2-carboxylic acid (FFCA); and
 (d) less than 1000 ppmw of alkyl 5-formylfuran-2-carboxylate (AFFC),
 all amounts are based on the total weight of the composition, and wherein the composition has a b* value of less than 4.

In another embodiment, the dried, solid composition comprises:
 (a) at least 70 wt % of 5-(methoxycarbonyl) furan-2-carboxylic acid (MCFC);
 (b) less than 30 wt % of furan-2,5-dicarboxylic acid (FDCA);
 (c) less than 500 ppmw of 5-formylfuran-2-carboxylic acid (FFCA); and
 (d) less than 500 ppmw of methyl 5-formylfuran-2-carboxylate (MFFC),
 all amounts are based on the total weight of the composition, and wherein the composition has a b* value of less than 4.

In yet another embodiment, the dried, solid composition comprises:
 (a) at least 99 wt % of 5-(methoxycarbonyl) furan-2-carboxylic acid (MCFC);
 (b) less than 500 ppmw of furan-2,5-dicarboxylic acid (FDCA);
 (c) less than 10 ppmw of 5-formylfuran-2-carboxylic acid (FFCA); and
 (d) less than 100 ppmw of methyl 5-formylfuran-2-carboxylate (MFFC),
 all amounts are based on the total weight of the composition, and
 wherein the composition has a b* value of −1 to +1.

In yet another embodiment, the dried, solid composition comprises:
 (a) at least 99 wt % of 5-(methoxycarbonyl) furan-2-carboxylic acid (MCFC);
 (b) less than 500 ppmw of furan-2,5-dicarboxylic acid (FDCA);

(c) less than 10 ppmw of 5-formylfuran-2-carboxylic acid (FFCA); and (d) less than 100 ppmw of methyl 5-formylfuran-2-carboxylate (MFFC), all amounts are based on the total weight of the composition, and wherein the composition has a b* value of −0.5 to +0.5.

In various embodiments, the dried, solid composition is obtained without performing or undergoing a reactive purification step.

In various other embodiments, the dried, solid composition is obtained without performing or undergoing a secondary oxidation step, a hydrogenation step, and/or a treatment step with an oxidizer.

In yet various other embodiments, the dried, solid composition is polymer grade, i.e., it has sufficient purity to be used for making a polymer without performing or undergoing a reactive purification step, such as a secondary oxidation step, a hydrogenation step, and/or a treatment step with an oxidizer.

To remove any doubt, the present invention includes and expressly contemplates and discloses any and all combinations of embodiments, features, characteristics, parameters, and/or ranges mentioned herein. That is, the subject matter of the present invention may be defined by any combination of embodiments, features, characteristics, parameters, and/or ranges mentioned herein.

It is contemplated that any ingredient, component, or step that is not specifically named or identified as part of the present invention may be explicitly excluded.

Any process/method, apparatus, compound, composition, embodiment, or component of the present invention may be modified by the transitional terms "comprising," "consisting essentially of," or "consisting of," or variations of those terms.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered as approximations, unless the context indicates otherwise. These values and ranges may vary from their stated numbers depending upon the desired properties sought to be obtained by the present disclosure as well as the variations resulting from the standard deviation found in the measuring techniques. Moreover, the ranges described herein are intended and specifically contemplated to include all sub-ranges and values within the stated ranges. For example, a range of 50 to 100 is intended to include all values within the range including sub-ranges such as 60 to 90, 70 to 80, etc.

Any two numbers of the same property or parameter reported in the working examples may define a range. Those numbers may be rounded off to the nearest thousandth, hundredth, tenth, whole number, ten, hundred, or thousand to define the range.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following working examples, although it should be understood that these examples are included merely for purposes of illustration and are not intended to limit the scope of the invention.

EXAMPLES

Analytical Techniques

Liquid Chromatographic Method for Sample Analysis

Samples were analyzed with an Agilent 1260 LC unit having a quaternary pump, an autosampler (3 uL injection), a thermostated column compartment (35° C.), and a diode array UV/vis detector (280 nm). The chromatograph was fitted with a 150 mm×4.6 mm Thermo Aquasil C18 column packed with 3-micron particles. The solvent flow program used is shown in the table below. Channel A was 0.1% phosphoric acid in water, channel B was acetonitrile, and channel C was tetrahydrofuran (THF).

| Time (min) | % A | % B | % C | Flowrate (mL/min) |
|---|---|---|---|---|
| Initial | 95.0 | 0.0 | 5.0 | 1.50 |
| 6 | 95 | 0 | 5.0 | 1.50 |
| 6.1 | 65 | 30 | 5.0 | 1.50 |
| 9 | 65 | 30 | 5.0 | 1.50 |
| 10.1 | 15 | 80 | 5.0 | 1.50 |
| 12 | 15 | 80 | 5.0 | 1.50 |
| 12.1 | 95 | 0 | 5.0 | 1.50 |
| 17 | 95 | 0 | 5.0 | 1.50 |

EZChrom elite was used for control of the HPLC and for data processing. A 5-point linear calibration was used in the (approximate) range of 0.25 to 100 ppm for FFCA, FDCA, MCFC, MMFC, and MFFC. Solid samples were prepared by dissolving ~0.05 g (weighed accurately to 0.0001 g) in 10 mL of 50:50 DMF/THF so that ppm levels of FFCA and MFFC could be detected. For purity analysis, the samples were further diluted by pipetting a 100 µL sample into a 10 mL volumetric flask and diluted to volume with 50:50 DMF/THF. Sonication was used to ensure complete dissolution of the sample in the solvent. For liquid samples, 0.1 g of sample was weight out and diluted to 10 mL with 50:50 DMF/THF. A small portion of the prepared sample was transferred to an auto sampler vial for injection onto the LC.

Color Measurement

1) Assembled the Carver Press die as instructed in the directions—placed the die on the base and placed the bottom 40-mm cylinder polished side face-up.

2) Placed a 40-mm plastic cup (Chemplex Plasticup, 39.7×6.4 mm) into the die.

3) Filled the cup with the sample to be analyzed. The exact amount of sample added is not important.

4) Placed the top 40-mm cylinder polished side face-down on the sample.

5) Inserted the plunger into the die. No "tilt" should be exhibited in the assembled die.

6) Placed the die into the Carver Press, making sure that it is near the center of the lower platen. Closed the safety door.

7) Raised the die until the upper platen made contact with the plunger. Applied >10,000 lbs. pressure. Then allowed the die to remain under pressure for approximately 30 seconds (exact time not critical).

8) Released the pressure and lowered the lower platen holding the die.

9) Disassembled the die and remove the cup. Placed the cup into a labeled plastic bag (Nasco Whirl-Pak 4 oz).

10) Using a HunterLab UltraScan Pro colorimeter, created the following method (Hunterlab EasyMatchQC software, version 3.6.2 or later):
   Mode: RSIN-LAV (Reflectance Specular Included)
   Area View: 0.78 in.
   UV Filter Position: Nominal
   Measurements:
      CIE L* a* b*
      CIE X Y Z 11) Standardized the instrument as prompted by the software using the light trap accessory and the certified white tile accessory pressed against the reflectance port.

12) Ran a green tile standard using the certified white tile and compared the CIE X, Y, and Z values obtained against the certified values of the tile. The values obtained should be ±0.15 units on each scale of the stated values.

13) Analyzed the sample in the bag by pressing it against the reflectance port and obtaining the spectrum and L*, a*, b* values. Obtained duplicate readings and average the values for reporting.

Examples 1-5

Air Oxidation of Methyl 5-Methylfuran-2-Carboxylate (MMFC)

The air oxidation of MMFC in an acetic acid solvent using a catalyst system containing cobalt, manganese, and bromine was carried out according to the general procedures below. The reaction is shown in equation 1:

General Procedures

Glacial acetic acid (125.7 g) and the catalyst components in the amounts described in Table 1 were transferred to a 300-mL titanium autoclave equipped with a high-pressure condenser, a baffle, and an Isco pump. Cobalt, manganese, and ionic bromine were provided as cobalt (II) acetate tetrahydrate, manganese (II) acetate, and aqueous hydrobromic acid (48.7 wt % in water), respectively.

The autoclave was pressurized with approximately 50 psig of nitrogen, and the homogeneous mixture was heated to the desired temperature in a closed system (i.e., with no gas flow) with stirring.

At the desired reaction temperature, an air flow of 1500 sccm was introduced at the bottom of the solution, and the reaction pressure was adjusted to the desired level. Liquid MMFC was fed at a rate of 0.20 mL/min via a high-pressure Isco pump (this is t=0 for the reaction time).

After 30 seconds from the start of the substrate feeding, 1.0 g of peracetic acid (32 wt % in acetic acid) in 5.0 g of acetic acid was introduced using a blow-case to start the reaction.

The feed was stopped after 1 h, and the reaction continued for an additional hour at the same conditions of air flow, temperature, and pressure.

After the reaction time was completed, the air flow was stopped, and the autoclave was cooled to room temperature and depressurized to obtain a heterogeneous mixture.

The heterogeneous mixture was filtered to isolate a white product. The mass of the filtrate was recorded. The white product was washed with 60 mL of acetic acid two times. The washed white product was oven dried at 110° C. under vacuum overnight, and then weighed. The solid product, the filtrate, and the acetic acid washes were analyzed by Liquid Chromatography.

The Off-gas was analyzed for CO and $CO_2$ by ND-1R (ABB, Advanced Optima) and $O_2$ by a paramagnetism detection system (Servomex, 1440 Model).

Figure 1:
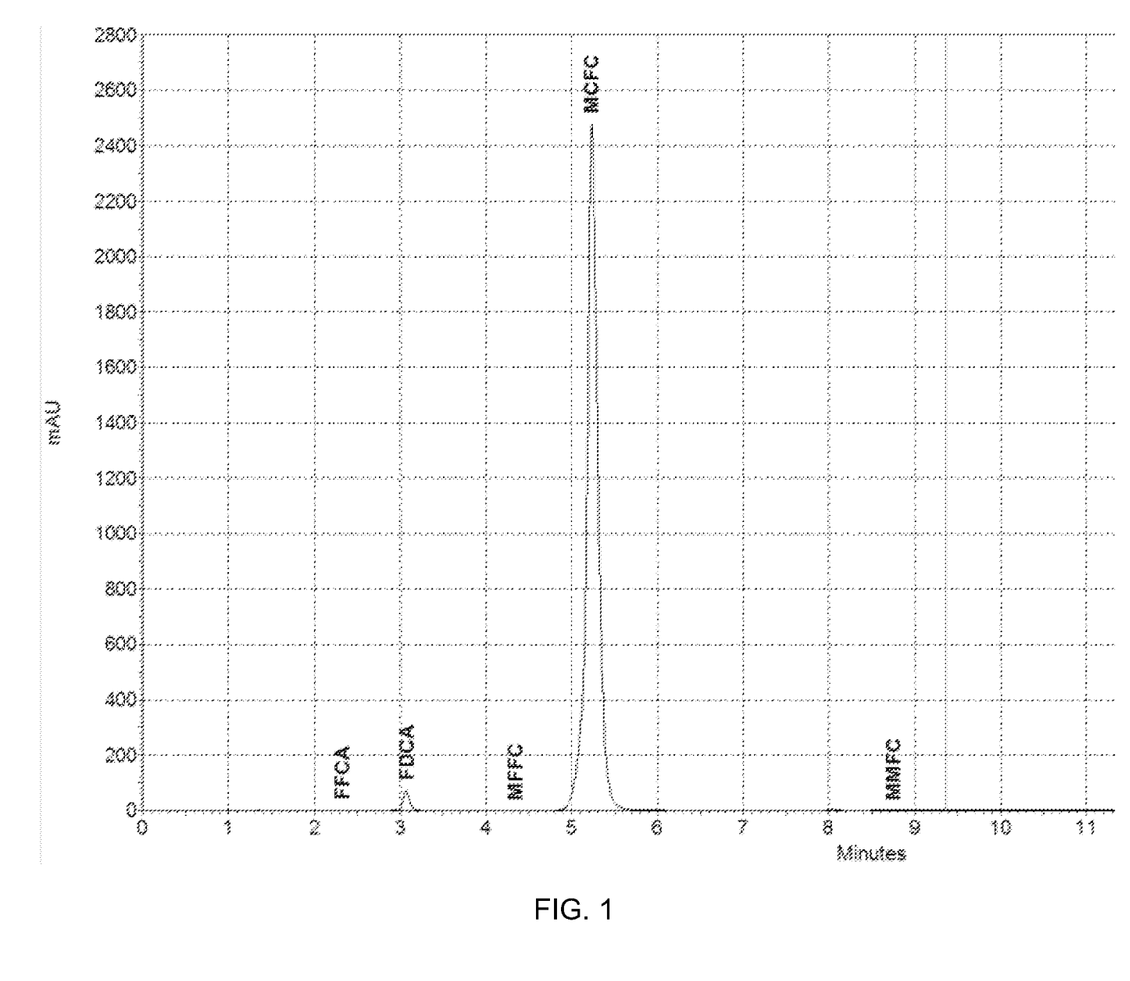
FIG. 1 is a chromatogram of the white, solid product from Example 3 by liquid chromatography.

The results are reported in Table 1. The LC chromatogram of the white, solid product from Example 3 is shown in the Figure.

TABLE 1

Results from Semi-Batch Oxidation of MMFC at Different Conditions

| | Example No. | | | | |
| --- | --- | --- | --- | --- | --- |
| | 1 | 2 | 3 | 4 | 5 |
| Temp. (° C.) | 110 | 132 | 132 | 155 | 170 |
| Pressure (psig) | 130 | 130 | 130 | 130 | 130 |
| Co(OAc)$_2$4H$_2$O (g) | 1.56 | 1.56 | 1.56 | 1.56 | 1.57 |
| Mn(OAc)$_2$ (g) | 0.054 | 0.060 | 1.081 | 0.050 | 0.050 |
| Aq. HBr[a] (g) | 0.92 | 0.93 | 0.91 | 0.93 | 0.92 |
| MMFC[b] (g) | 13.1 | 13.1 | 13.1 | 13.1 | 13.1 |
| MMFC Conversion (%) | 99.39 | 99.94 | 99.93 | 99.95 | 99.98 |
| MCFC Yield[c] (%) | 77.6 | 84.7 | 77.6 | 75.62 | 52.5 |
| FDCA Yield[c] (%) | 0.2 | 1.7 | 1.5 | 6.6 | 15.2 |

TABLE 1-continued

Results from Semi-Batch Oxidation of MMFC at Different Conditions

| | Example No. | | | | |
|---|---|---|---|---|---|
| | 1 | 2 | 3 | 4 | 5 |
| Solid Product Composition | | | | | |
| MCFC (wt %) | 99.39 | 98.44 | 97.56 | 94.65 | 72.63 |
| FDCA (wt %) | 0.036 | 1.34 | 1.15 | 5.29 | 27.26 |
| MFFC (ppmw) | 2504.6 | 95.7 | 379.8 | 123.3 | 246.6 |
| FFCA (ppmw) | 5.4 | 1.71 | 318.6 | 0 | 0.002 |
| b* | 0.34 | −0.11 | 0.62 | 0.15 | −0.59 |
| CO (total mol) | 0.008 | 0.008 | 0.011 | 0.012 | 0.01 |
| $CO_2$ (total mol) | 0.06 | 0.051 | 0.008 | 0.065 | 0.107 |
| $CO_x$ (total mol) | 0.000283 | 0.000246 | 0.000079 | 0.000321 | 0.000488 |

$^a$= 48.7 wt % in water;
$^b$= 97.8 wt % purity;
$^c$= in solid, filtrate, and AA washes

As seen from Table 1, the oxidation reaction mainly formed MCFC, instead of FDCA. This reaction produces water as a byproduct, but surprisingly, under certain conditions, hydrolysis of the methyl ester bond by the water to make FDCA was very minimal.

It is also worth noting from Table 1 that it is possible to produce a high-purity product with an FFCA level of only 1.71 ppmw, an MFFC level of only 95.7 ppmw, and a b* level of ×0.11 in one (main) oxidation step. FFCA and MFFC are known chain terminators in a polymerization process. At such low levels of impurities and color, this product can be used directly to make a polymer without further purification. That a polymer grade monomer can be made with no additional purification steps has significant economic advantages.

The invention has been described in detail with particular reference to specific embodiments thereof, but it will be understood that variations and modifications can be made within the spirit and scope of the invention.

I claim:

1. A process for preparing a furan-2,5-dicarboxylic acid (FDCA) compound of the structural formula (I):

(I)

the process comprising:
(a) reacting a compound of the structural formula (II):

(II)

with an oxidizing agent in a reactor comprising an oxidation catalyst and a solvent; and
(b) removing water vapor from the reactor while the reaction is occurring, wherein:
the oxidation catalyst comprises cobalt, manganese, and bromine;
the solvent comprises a monocarboxylic acid having 2 to 6 carbon atoms;
$R^1$ is hydrogen, $R^{30}$—, or $R^3C(O)O$—;
$R^2$ is an alkyl group having 1 to 6 carbon atoms; and
$R^3$ is hydrogen or an alkyl group having 1 to 6 carbon atoms.

2. The process according to claim 1, wherein $R^3$ is hydrogen or an alkyl group having 1 to 3 carbon atoms, and $R^2$ is an alkyl group having 1 to 3 carbon atoms.

3. The process according to claim 1, wherein $R^1$ is hydrogen and $R^2$ is methyl.

4. The process according to claim 3, wherein the oxidizing agent is oxygen, air, or other oxygen-containing gas.

5. The process according to claim 4, wherein the reacting step is conducted at a temperature of 100° C. to 200° C.

6. The process according to claim 5, wherein the reacting step is conducted at a pressure of 50 psig to 1000 psig.

7. The process according to claim 6, wherein the solvent comprises acetic acid.

8. The process according to claim 7, wherein the bromide is derived from hydrobromic acid or sodium bromide.

9. The process according to claim 8, wherein the weight ratio of Co:Mn ranges from 0.1:1 to 100:1.

10. The process according to claim 9, wherein the yield of compound (I) is at least 80.

11. The process according to claim 10, wherein the yield of furan-2,5-dicarboxylic acid (FDCA) is less than 20.

12. The process according to claim 11, wherein the removing step comprises withdrawing a gaseous stream comprising solvent vapor and water vapor from the reactor.

13. The process according to claim 12, which further comprises:
separating water from the solvent in the gaseous stream; and
recycling the solvent to the reactor.

14. The process according to claim 12, which further comprises:
condensing the gaseous stream to form a liquid comprising water and solvent;
separating water from the solvent in the liquid; and
recycling the solvent to the reactor.

15. The process according to claim 13, wherein the solvent comprises 2 wt or less of water at the end of the reaction, based on the total weight of the solvent.

16. The process according to any one of claim 1, wherein the reacting step is conducted at a pressure lower than the vapor pressure of water at the reaction temperature to evaporate at least a portion of the water formed by the reaction.

17. The process according to claim 16, wherein a portion of the solvent is evaporated along with the water formed by the reaction.

18. The process according to claim 17, which produces less FDCA compared to a process carried out under the same reaction conditions but without performing step (b).

* * * * *